(12) United States Patent
Okuno (10) Patent No.: US 8,767,913 B2
(45) Date of Patent: Jul. 1, 2014

(54) X-RAY RADIOGRAPHY DEVICE

(75) Inventor: Tomoharu Okuno, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 390 days.

(21) Appl. No.: 13/312,192

(22) Filed: Dec. 6, 2011

(65) Prior Publication Data

US 2013/0142306 A1    Jun. 6, 2013

(51) Int. Cl.
*A61B 6/08* (2006.01)
*G01N 23/04* (2006.01)

(52) U.S. Cl.
CPC ..................................... *G01N 23/04* (2013.01)
USPC ............................................ 378/62; 378/206

(58) Field of Classification Search
CPC ...... A61B 6/0306; A61B 6/482; A61B 6/484; A61B 6/504; G01N 23/04
USPC .......................................... 378/62, 205–207
See application file for complete search history.

(56) References Cited

U.S. PATENT DOCUMENTS

2011/0164728 A1* 7/2011 Tsuchiya et al. ................ 378/62

FOREIGN PATENT DOCUMENTS

| JP | 2004-358254 A | 12/2004 |
| JP | 2007-135692 A | 6/2007 |
| JP | 2007-185209 A | 7/2007 |

* cited by examiner

*Primary Examiner* — Irakli Kiknadze (74) *Attorney, Agent, or Firm* — McDermott Will & Emery LLP (57) ABSTRACT

In long-format radiography, a long-format imaging region is determined and the long-format imaging region is partitioned into a plurality of imaging regions. Following this, and prior to x-ray imaging, a particular location of an overlapping image area is illuminated by a laser line marker, through laser line marker emission controlling means, in order to confirm that no overlapping image area, which is provided in adjacent imaging regions when the long-format imaging region is partitioned, is positioned on a location of interest of the examination subject. The ability to indicate clearly the particular location of the overlapping image area, through the laser line marker, makes it possible to evaluate accurately whether or not an overlapping image area is positioned on a location of interest. Doing so makes it possible to set the imaging region easily.

6 Claims, 6 Drawing Sheets

X-RAY RADIOGRAPHY DEVICE

CROSS REFERENCE TO RELATED APPLICATION

This application is based on Japanese Patent Application No. 2009-159765 filed Jul. 6, 2009, which is incorporated herein by reference. This application was published Jan. 20, 2011 as JP 2011-010992.

FIELD OF TECHNOLOGY

The present invention relates to an x-ray radiography device for capturing an x-ray image, and, in particular, relates to a long-format radiography technology for obtaining a plurality of concatenated x-ray images, where the plurality of x-ray images is concatenated together through image processing to obtain a single long-format image that is an image of a wide format.

BACKGROUND

In recent years long-format images wherein a plurality of x-ray images is captured and concatenated together to obtain a single x-ray image have become widely popular as a method for imaging locations (such as the entire spinal column or the entire leg) that are larger than the detecting surface in the x-ray equipment (See Japanese Unexamined Patent Application Publication 2004-358254, Japanese Unexamined Patent Application Publication 2007-135692 and Japanese Unexamined Patent Application Publication 2007-185209).

In long-format radiography, first an imaging distance between the subject and the x-ray tube is kept constant, the long-format imaging region is determined, and then each individual imaging region is determined through partitioning into regions that fit into the detector field of the x-ray detector. Partitioning into individual imaging regions is performed so that adjacent imaging regions overlap. Moreover, shifting the partitioned imaging region with each imaging cycle makes it possible to obtain a plurality of concatenated x-ray images. A single x-ray image is obtained through image processing on the regions wherein there are overlapping x-ray images, to concatenate them together.

However, this type of long-format radiography has problems such as the following. In x-ray radiography, when imaging a long-format imaging region continuously, there will be variability in the image quality, such as in the consistency within the area that is imaged, so that when image processing is performed to overlap adjacent x-ray images, the image quality of the overlapping imaged areas will suffer, making the image difficult to read. For example, when performing long-format imaging with the entirety of the lower extremities, as the imaging region, in a state wherein there is a load on the knees in order to perform a radiographic examination focusing on the knee joint portion along with understanding and the lower extremities as a whole, if the overlapping image area is at the knee joint portion that is the location of interest in the examination, then it will be necessary to perform the radiological examination of the hip joint portion using an x-ray image that has reduced quality. Moreover, because the overlapping image area in adjacent images in the long-format imaging region is imaged twice, this can lead to increased impact on those locations that should be protected from x-rays (such as the reproductive system). Given this reasoning, it is desirable to eliminate from the overlapping image areas in adjacent images locations of interest, such as the locations one wishes to examine, locations for which one wishes to minimize the x-ray exposure, and the like. Sometimes the x-ray radiography must be performed again if the location of interest is in the overlapping image area. Because of this, it is desirable to protect the patients from excessive x-ray exposure in advance.

The present invention was created in contemplation of such circumstances, and the object thereof is to provide an x-ray radiography device wherein it is possible to confirm accurately, prior to the x-ray radiography, whether or not the overlapping image area in adjacent imaging regions is not provided at a location of interest of the examination subject.

SUMMARY

The following understandings were obtained by the inventor in the present application as a result of earnest research. Namely, prior to x-ray radiography, the operators use a collimator lamp to confirm optical illumination of the entirety of each individual imaging region, checking the imaging regions one by one at each imaging location. However, in long-format imaging, a plurality of x-ray images are joined together, and thus it is necessary to control distortion of the individual x-ray images, and so typically it is necessary to increase the imaging distance (to about 2 to 3 m). Because of this, in the optical illumination using the collimator lamp, the beam is scattered so the edges of the imaging region that are illuminated to become blurred, making such checks difficult. This is true even when the room where the imaging is to occur is darkened. That is, it is difficult to identify, through optical illumination with a collimator lamp, whether or not an overlapping image area that is provided in adjacent imaging regions is provided at a location of interest of the examination subject, and thus it has not been possible to establish the imaging region easily.

The present invention is based on the understandings set forth above, and it takes the following form in order to achieve the object thereof. The x-ray radiography device according to the present invention comprises: an x-ray tube for emitting an x-ray toward an examination subject, with an attached collimator for adjusting the field of irradiation of the x-ray; an x-ray detection device for detecting x-rays that have traversed the examination subject; a laser line marker for emitting a laser beam that is emitted in the form of a line that, when viewed from the x-ray tube, is perpendicular to the bodily axis of the examination subject; imaging region partitioning means for partitioning, into a plurality of imaging regions, a long-format imaging region that has been set, so that there will be overlapping image areas wherein portions of adjacent imaging regions overlap; and laser line marker emission controlling means for controlling the emission of a laser beam from the laser line marker onto the overlapping image areas, by calculating the overlapping image areas based on location data for the plurality of imaging regions that have been partitioned by the imaging region partitioning means.

Given the x-ray radiography device according to the present examples, particular locations of the overlapping image areas are illuminated by the laser line marker, making it possible to check whether or not an overlapping image area that is provided at adjacent imaging regions when partitioning a long-format imaging region into a plurality of imaging regions is provided at a location of interest of the examination subject. The use of the laser line marker makes it possible to illuminate clearly particular locations of the overlapping image areas in adjacent imaging regions, even when the imaging region is far away. As a result, it is possible to evaluate accurately whether or not the overlapping image area is provided at a location of interest of the examination subject, thus making it possible to set the imaging region easily.

Moreover, in one example of an x-ray radiography device according to the present examples, the particular location of the overlapping image area is an edge portion of the overlapping image area. The ability to illuminate clearly, with the laser line marker, the edge portion of the overlapping image area makes it is possible to identify more accurately whether or not the overlapping image area is provided at a location of interest.

Moreover, in one example of an x-ray radiography device according to the present examples, the particular location of the overlapping image area is a center point of the overlapping image area. The ability to illuminate clearly, with the laser line marker, the center point of the overlapping image area makes it is possible to identify more accurately whether or not the overlapping image area is provided at a location of interest. Moreover, when compared to the method of illuminating an edge portion of the overlapping image area, this makes it possible to reduce the frequency of illumination.

Additionally, in one example of an x-ray radiography device according the present examples, x-ray tube angle changing means for changing the direction of emission of the laser beam of the laser line marker by changing the angle of the x-ray tube centered on the focal point of the x-ray emission is provided. This makes it possible to accommodate x-ray radiography devices wherein the individual imaging regions are imaged sequentially while changing the angle of the x-ray tube around the focal point of the x-ray emissions of the x-ray tube.

In one example of an x-ray radiography device, x-ray tube moving means are also provided for moving the laser line marker laser beam illuminated position by moving the x-ray tube in the direction parallel to the direction of movement of the x-ray detecting device. Doing so makes it possible to accommodate an x-ray radiography device wherein the individual imaging regions are imaged while moving the x-ray tube parallel to the direction of motion of the x-ray detecting device.

Moreover, in the x-ray radiography device according to the present examples, the laser line marker may be structured from a plurality of laser line markers, and preferably each of the different particular locations of the overlapping image areas are illuminated. Because it is possible to illuminate each of the different particular locations of the overlapping image areas through the plurality of laser line markers, it is possible to check a plurality of locations simultaneously. Moreover, this makes it possible to reduce the number of checks, depending on the number of laser line markers.

The x-ray radiography device according to the present invention illuminates, with a laser line marker, a particular location of an overlapping image area, in order to check whether or not the overlapping image area, which is provided in adjacent imaging regions, is provided at a location of interest of the examination subject, when partitioning a long-format imaging region into a plurality of imaging regions. The use of the laser line marker makes it possible to illuminate clearly the particular location of the overlapping image area at adjacent imaging regions, even when the imaging region is far away. As a result, it is possible to evaluate accurately whether or not an overlapping image area is provided at a location of interest, thus making it easy to set the imaging regions.

DETAILED DESCRIPTION

Figure 1:
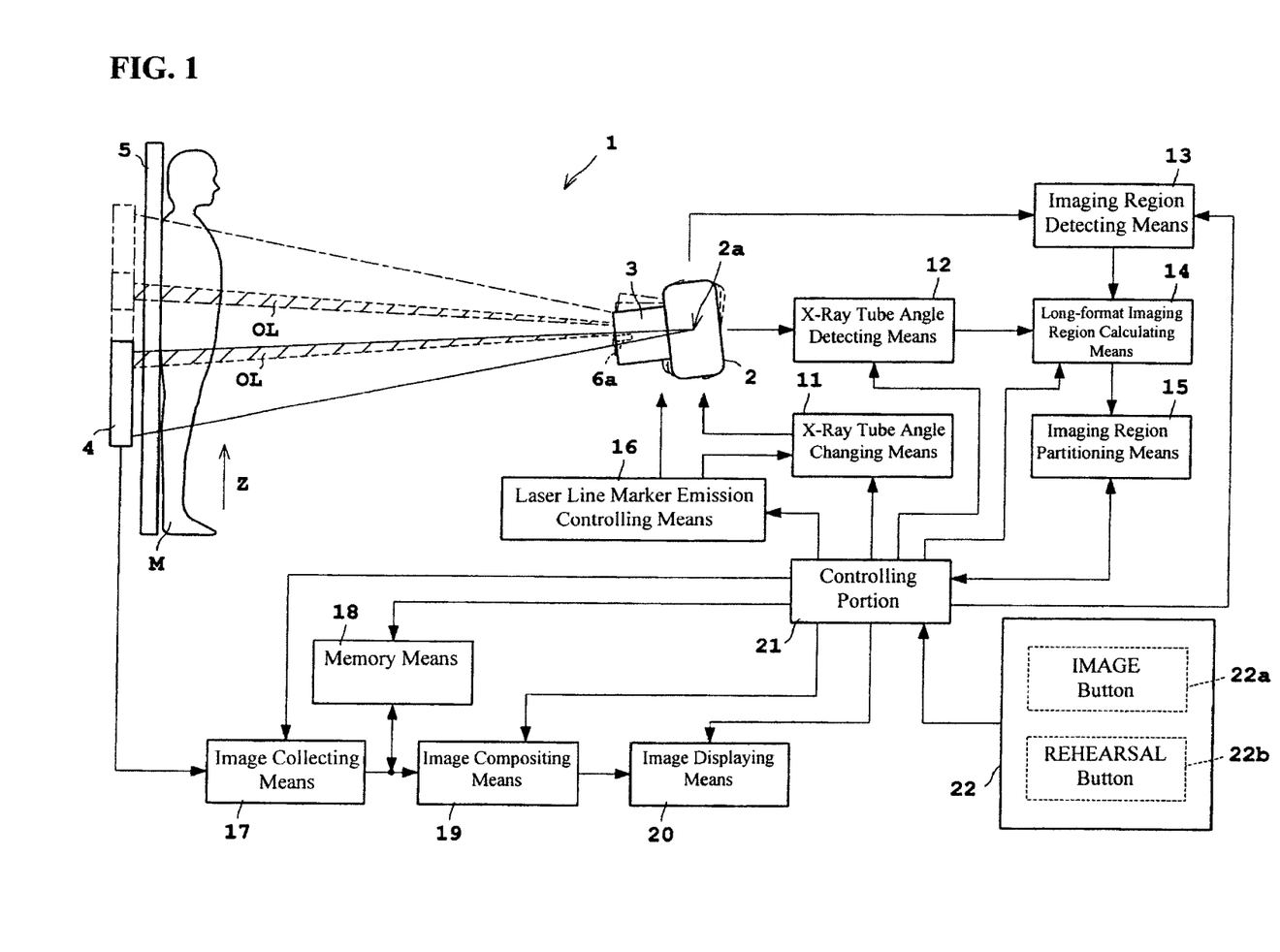
FIG. 1 is a block diagram illustrating an x-ray radiography device according to an example.
Figure 2:
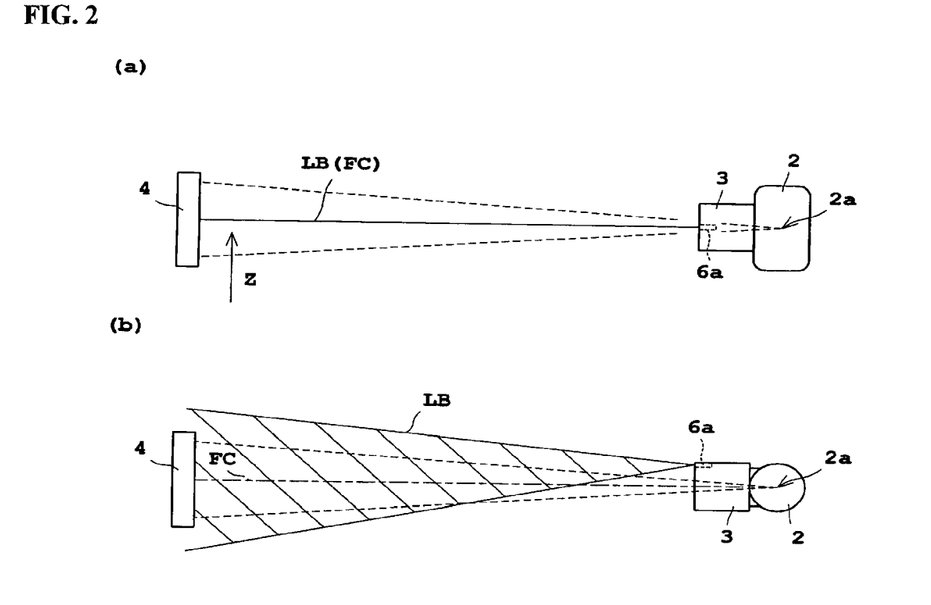
FIG. 2 is drawings that are provided for explaining the laser light marker illumination regarding the example, wherein (a) is a side view and (b) is a top view.
Figure 3:
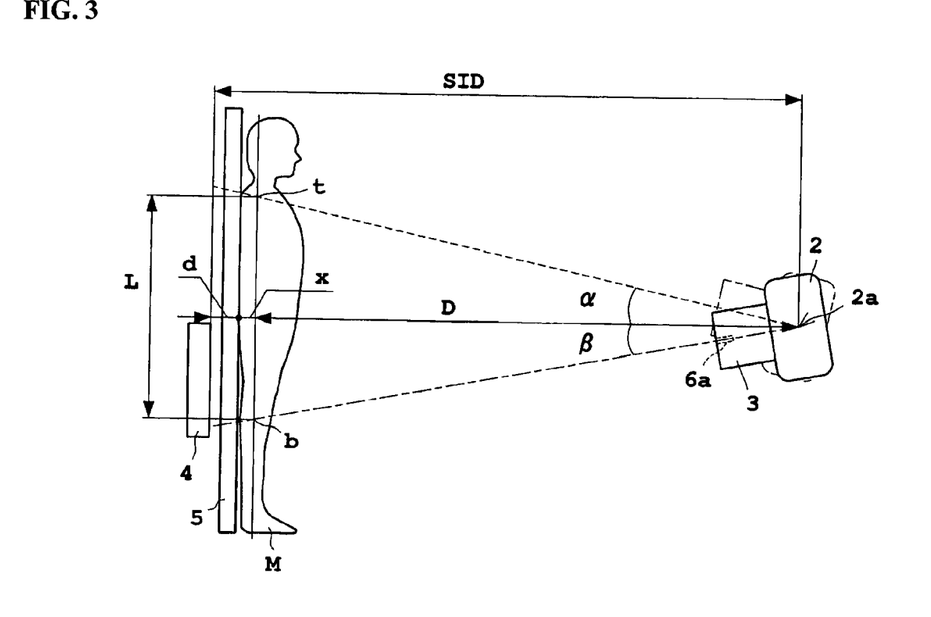
FIG. 3 is a diagram for providing an explanation of the method for determining the long-format imaging region in the example.

An example is explained below referencing the figures. FIG. 1 is a block diagram illustrating an x-ray radiography device according to the example. FIG. 2 is drawings that are provided for explaining the laser light marker illumination, wherein (a) is a side view and (b) is a top view. Moreover, FIG. 3 is a diagram for providing an explanation of the method for determining the long-format imaging region in the example.

FIG. 1 will now be referenced. The x-ray radiography device 1 includes an x-ray tube 2 for emitting an x-ray toward an examination object M; a collimator 3, attached to the emitting side of the x-ray tube 2, for adjusting the field of x-ray radiation emitted from the x-ray tube 2; a flat-panel-type x-ray detecting device (hereinafter abbreviated "FPD") 4, for detecting x-rays that have traversed the examination subject M; and a partition wall 5 (which is a table if the examination subject M is lying) for constraining the standing position of the examination subject M.

The collimator 3 is provided with a leaf, not shown, for adjusting the field of the radiation of the x-rays that are emitted from the x-ray tube 2. The leaf is provided with two sets of mutually paired leafs, where these two sets are disposed crossing each other. The leafs that are disposed facing each other are able to adjust the field of irradiation through increasing or decreasing the width. Moreover, as illustrated in FIG. 2, a laser line marker 6a is attached to the x-ray-emission side of the collimator 3. As illustrated in FIG. 2(a) the laser beam LB that is emitted from the laser line marker 6a is emitted so as to pass through the center line FC of the x-ray flux that is emitted from the x-ray tube 2, and so as to be perpendicular, when viewed from the x-ray tube 2, relative to the bodily axis (the Z direction) of the examination subject M. Moreover, as illustrated in FIG. 2(b), the laser beam LB from the laser line marker 6a illuminates in a line shape on the examination subject M, through being emitted in a fan shape. Note that this laser line marker 6a usually would be used when setting the region while illuminating the top end (the starting position) t, or the bottom end (the ending position) b of the long-format imaging region L.

FIG. 1 will be referenced. The FPD 4 is structured so as to move linearly in the direction that is parallel to the bodily axis of the examination subject M (the vertical direction). The FPD 4 is provided with a moving mechanism, not shown, so as to be able to move in accordance with the region of irradiation that is the irradiated with x-rays by the x-ray tube 2. Note that the FPD 4 corresponds to the x-ray detecting device in the claims.

Moreover, the x-ray radiography device 1 has x-ray tube angle changing means 11 for changing the angle of the x-ray tube 2, and x-ray tube angle detecting means 12 for detecting the angle of the x-ray tube 2, so as to be able to know the direction of the emission of the x-ray tube 2. The x-ray tube angle changing means 11 change the angle of the x-ray tube 2 through rotating around the center point 2a of the x-ray emission, as an axis that is in the direction that is parallel to the direction that is perpendicular, when viewed from the x-ray tube 2 side, relative to the bodily axis of the examination subject M.

FIG. 1 and FIG. 3 will be referenced. Moreover, the x-ray illuminating device 1 includes imaging distance detecting means 13 for detecting the observation distance D from the focal point 2a of the x-ray emission of the x-ray tube 2 to the plane of observation of an examination subject M; imaging region partitioning means for partitioning the long-format imaging region L into a plurality of imaging regions; and laser line marker emission controlling means 16 for controlling the emission of the laser line marker 6a and the direction of emission thereof.

The imaging distance detecting means 13 detect the imaging distance D from the values of a distance SID from the focal point 2a of the x-ray emission of the x-ray tube 2 to the detecting surface of the FPD 4, a distance d from the detecting surface of the FPD 4 to the surface of the screen 5, a distance x from the surface of the screen 5 to the plane of observation of the examination subject M. The distance SID will be changed by the moving mechanism, not shown, and normally is detected using a potentiometer. The distance d is a constant value, a value that is determined through being inputted, or the like, in advance. Moreover, the distance x is determined through a value that is inputted by the operator through an operating panel 22. Note that the imaging distance detecting means 13 detect the imaging distance D through D=SID−(d+x).

The long-format imaging region calculating means 14 illuminate, through the laser line marker 6a, the top end position t and bottom end position b of the long-format image, and calculate the long-format imaging region L based on the angles α and β of the x-ray tube 2, detected by the x-ray tube angle detecting means 12, and the imaging distance D from the focal point 2a of the x-ray emission from the x-ray tube 2 to the observation plane of the examination subject M.

The imaging region partitioning means 15 partition the long-format imaging region L, calculated by the long-format imaging region calculating means 14, into a plurality of imaging regions, so as to have overlapping image areas OL where portions of adjacent imaging regions overlap area.

The laser line marker imaging controlling means 16 calculate particular locations for the imaging region overlapping areas OL based on the position data for the plurality of imaging regions that were partitioned by the imaging region partitioning means 15, and control the illumination by the laser line marker 6a of the particular locations of the overlapping image areas OL to enable checking as to whether or not the overlapping image areas OL are placed on locations of interest of the examination subject. Note that the laser line marker emission controlling means 16 perform control that varies the angle of the x-ray tube 2, through the x-ray tube angle changing means 11, so as to illuminate the particular location with the laser line marker 6a.

Referencing FIG. 1. Moreover, the x-ray radiography device 1 has image collecting means 17 for collecting x-ray image data from the FPD 4; memory means 18 for storing, temporarily, the x-ray image data collected by the image collecting means 17; image compositing means 19 for compositing the continuous plurality of x-ray image data that are stored in the memory means 18 while identifying the overlapping image area OL of adjacent x-ray image data, to perform image processing into a single long-format image data; an image displaying means (for example, a monitor) 20 for displaying the long-format image data that has been produced by the image processing by the image compositing means 19.

Furthermore, the x-ray radiography device 1 further includes a controlling portion 21 for the overall control of the individual mechanisms; and an operating panel 22 through which it is possible for an operator to input settings, and the like, in the x-ray imaging. The operating panel 22 comprises: an IMAGE button 22a for executing the x-ray imaging; and a REHEARSAL button 22b for causing illumination of a laser beam LB from the laser line marker 6a to a particular location in the overlapping image area OL in order to identify whether or not an overlapping image area OL that is provided in adjacent imaging regions is provided at a location of interest.

The long-format imaging is performed by the x-ray radiography device 1 having the structures set forth above.

Figure 4:
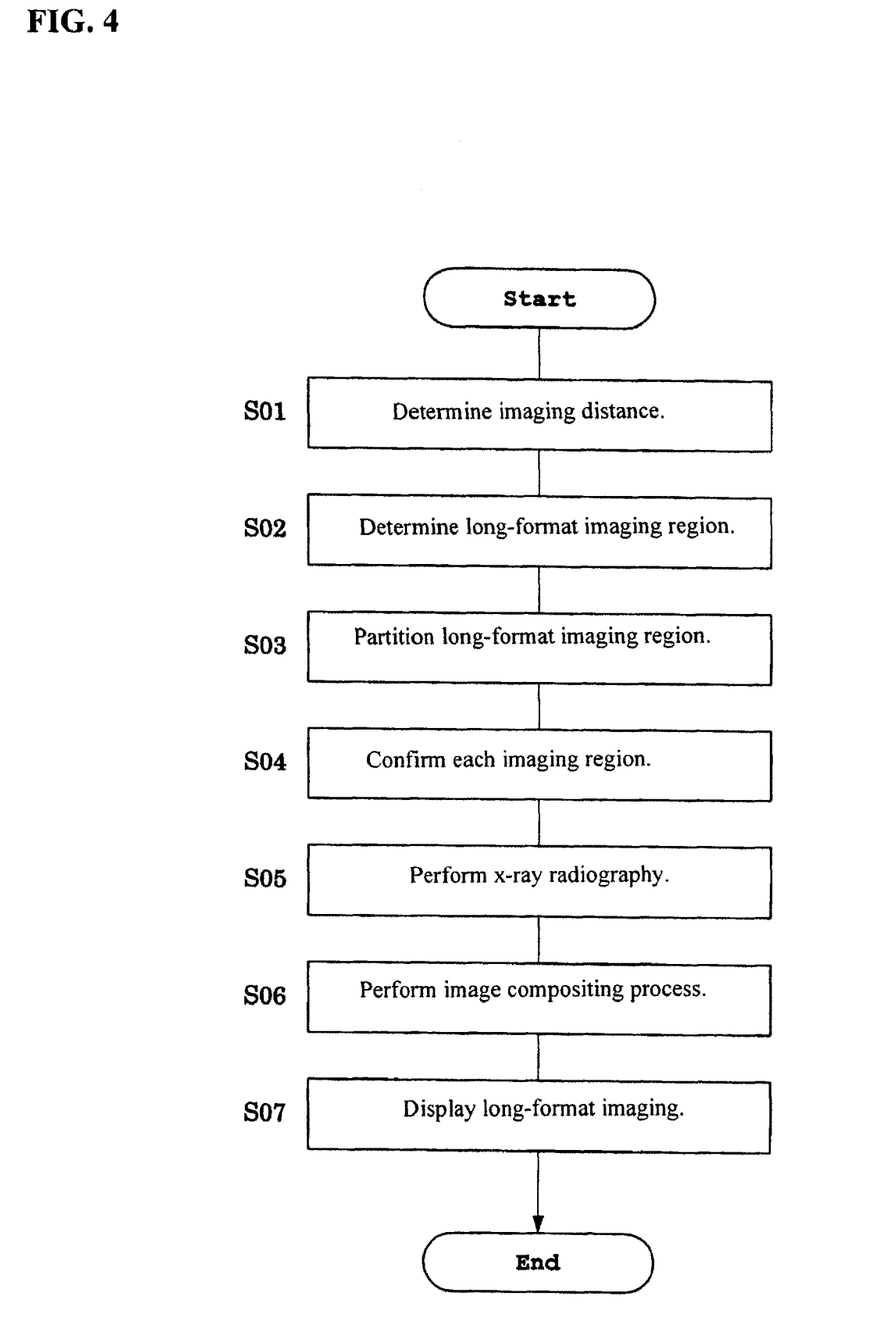
FIG. 4 is a flowchart showing the x-ray radiography method according to the example.
Figure 5:
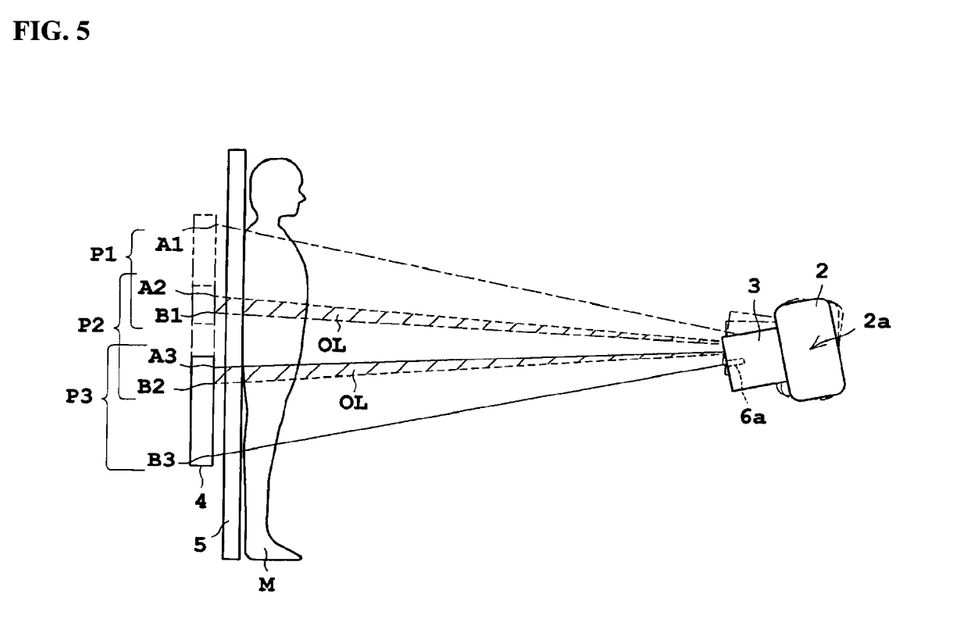
FIG. 5 is a diagram for providing an explanation of the laser line marker of the example.

The imaging method for long-format imaging in the x-ray radiography device 1 will be explained next. Note that FIG. 4 is a flowchart illustrating a long-format radiographic imaging method. FIG. 5 is a diagram for providing an explanation of the laser line marker. Note that the explanation will be while referencing FIG. 1 and FIG. 4, following which the other figures will be referenced as necessary.

(Step S01) Determining the Imaging Distance

FIG. 3 will be referenced. The imaging distance D from the focal point 2a of the x-ray emission of the x-ray tube 2 to the observation plane of the examination subject M is determined. Specifically, the distance from the focal point 2a of the x-ray emission of the x-ray tube 2, when a line is drawn so as to be normally incident to an observation plane (for example, the plane wherein there is the backbone, in the case that the subject of the observation is the entirety of the backbone of the examination subject M) that is at the position to be imaged in the examination subject M, parallel to the detecting surface of the FPD 4, where the distance between the focal point 2a and the observation plane of the examination subject M is the imaging distance D. The imaging distance D is detected through D=SID−(d+x) from the distance SID from the focal point 2a of the x-ray emission to the detecting surface of the FPD, the distance d from the detecting surface of the FPD 4 to the front face of the screen 5, and the distance x from the front face of the screen 5 to the observation plane of the examination subject. Moreover, this imaging distance D is a constant.

(Step S02) Determining the Long-Format Imaging Region

The long-format imaging region L is determined after determining the imaging distance D. The long-format imaging region L is determined through changing the angle of the x-ray tube 2 around the focal point 2a, to direct the laser beam LB from the laser line marker 6a of the collimator 3, which is attached to the x-ray emitting side of the x-ray tube 2 towards the examination subject M, to specify the top position t and the bottom position b. The laser beam LB illuminates in a line shape so as to be perpendicular, when viewed from the x-ray tube 2 side, to the direction of movement of the FPD 4. Given this, the positioning is determined while shining the laser beam LB onto the top end position of the examination subject M, and specifying the top end position t by pressing position determining buttons, not shown, in the operating panel 22.

When this is done, the x-ray tube angle detecting means 12 detect the angle α of the x-ray tube 2, in a state wherein the laser beam LB is directed onto the top end position t, through an electric signal of the information that the position determining button is pushed similarly, positioning is determined while the laser beam LB shines onto the bottom end position b of the examination subject M, and the bottom end position b is specified by pressing a position determining button, not shown. When this is done, the x-ray tube angle determining means 12 detect the angle β of the x-ray tube 2. Given this, the long-format imaging region calculating means 14 calculate and determine the long-format imaging region L geometrically from the angles α and β of the x-ray tube 2 and from the aforementioned imaging distance D.

(Step S03) Partitioning the Long-Format Imaging Region

FIG. 5 will be referenced. After determining the long-format imaging region L, then the long-format imaging region L is partitioned into a plurality of imaging regions. The partitioning of the long-format imaging region L partitions into a plurality of imaging regions that are each within a region wherein the x-rays that traverse the examination subject M can be contained within the detecting surface of the FPD 4. At this time, an overlapping image area OL is established (for example, 2 to 3 cm) so that adjacent imaging regions will overlap partially. The partitioning of the long-format imaging region L may instead be by, for example, specifying a number of partitions and then partitioning into equally spaced imaging regions. Note that in the present example the explanation is for the case of an imaging region that is partitioned in three.

(Step S04) Checking Each Individual Imaging Region

After the long-format imaging region L has been partitioned, then in order to confirm that the overlapping image areas OL that are provided at adjacent imaging regions are not provided at locations that one wishes to view in particular, or at locations of interest, such as locations for which one would wish to control the x-ray irradiation, the particular locations of the overlapping image areas OL are illuminated by the laser line marker 6a. The illumination by the laser line marker 6a is performed based on the information when the REHEARSAL button 22b of the operating panel 22 has been pressed. Here the explanation is for the method wherein the particular location of the overlapping image area OL that is illuminated by the laser line marker 6a is the edge portion of the overlapping image area OL, that is, the edge portion of each of the x-ray imaging regions.

When the REHEARSAL button 22b of the operating panel 22 is pressed, information that the REHEARSAL button 22b has been pressed is sent through the controlling portion 21 to the laser line marker emission controlling means 16. The laser line marker emission controlling means 16, based on the position data for the plurality of partitioned regions, partitioned by the imaging region partitioning means 15, illuminate one edge portion A1, that is, the top end position t, of the first imaging region P1 using the laser line marker 6a, as illustrated in FIG. 5. Given this, the operator is able to check the edge portion A1 at this time.

Moreover, the other edge portion B1 of the first imaging region P1 is illuminated based on the information that the REHEARSAL button 22b has been pressed again. Moreover, in the same way, the second position A2 is illuminated based on the information that the REHEARSAL button 22b has been pressed again, and this is repeated to sequentially illuminate the position B2, then the position A3, and then the position B3 (the bottom end position b), enabling the operator to check each of the positions. The edge portions of the overlapping image areas OL are illuminated in this way, making it possible to evaluate accurately whether or not an overlapping image area OL that is provided at adjacent imaging regions is provided at a location of interest of the examination subject M, making it possible to set the imaging regions easily.

Note that when a location of interest is within an overlapping image area OL, then processing is returned to Step S03 for partitioning the long-format imaging region and if, for example, there had been two partitions, then instead three partitions may be used to cause the overlapping image area OL to be away from the location of interest of the examination subject M.

(Step S05) X-Ray Imaging

The x-ray imaging is started after all of the imaging regions have been checked. As illustrated in FIG. 5, the x-ray imaging is performed sequentially, in the direction from the top end position t to the bottom end position b, on the plurality of imaging regions (P1, P2, and P3) that have been partitioned by the imaging region partitioning means 15. The x-ray imaging is performed based on information that the IMAGE button has been pushed in the operating panel 22. The x-ray imaging performs imaging by changing the angle of the x-ray tube 2 through the x-ray tube angle changing means 11 to direct the x-rays, and then to imaging, such as performing the x-ray radiography on the first imaging region P1. After this, then the x-ray irradiation and imaging is performed by changing to the respective angles that emit x-rays toward the second imaging region P2 and the third imaging region P3. At the time of the x-ray imaging, the FPD 4 moves to the respective positions of the imaging regions for each time. The x-rays that are emitted from the x-ray tube 2 traverse the examination subject M to be incident on the FPD 4. They are converted into electric signals by the FPD 4 based on the x-rays that are incident. The electric signals for the converted x-ray image data are collected by the image collecting means 17 and stored temporarily in the memory means 18.

(Step S06 and S07) Image Compositing Process and Displaying the Long-format Image The x-ray image data for the plurality of images, stored temporarily in the memory means 18, are read out and the overlapping image areas OL in the x-ray image data are subjected to image processing, to cause the continuous x-ray image data that was imaged in multiple partitions into a single long-format image data. Given this, the long-format image data is displayed on the image displaying means 20. Note that the long-format image data may be used on other devices, such as PCs, through a network.

The x-ray radiography device as described above makes it possible to illuminate clearly the overlapping image areas OL within adjacent imaging regions, even when the imaging regions are far away, through the use of the laser line marker 6a for checking whether or not an overlapping image area that is provided at adjacent imaging regions of the long-format imaging region L are provided at a location of interest of the examination object M. Moreover, it is possible to evaluate more clearly whether or not an overlapping image area OL that is provided at adjacent imaging regions is provided at a location of interest of the examination subject M, through illuminating clearly the edge portions of the long-format imaging region L. Consequently, the imaging regions can be set easily.

Additionally, the positioning can be checked without darkening the imaging room, thus making it possible to check the imaging regions without causing the subject M to worry about the time of imaging. Moreover, the laser line marker 6a has a long-format service life when compared to a collimator lamp, which is used conventionally, making it possible to extend the product service life of the equipment as a whole.

Figure 6:
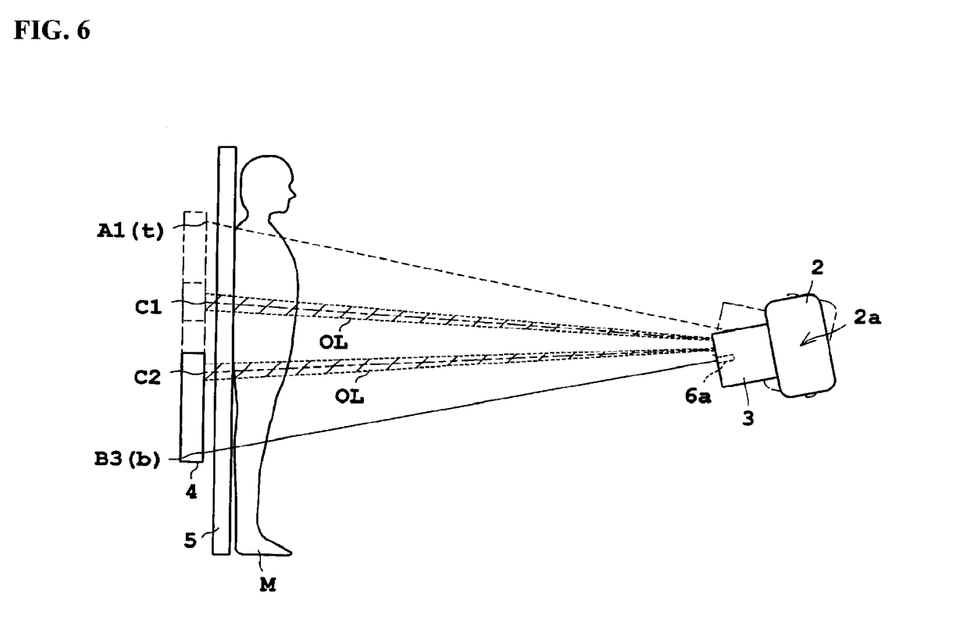
FIG. 6 is a diagram for providing an explanation of the laser line marker of another example.

Another example is explained next in reference to the figures. FIG. 6 is a diagram for providing an explanation of the laser line marker of the second example of embodiment.

While in the above example the method was one wherein the edge portions of the overlapping image areas were illuminated as particular locations of the overlapping image areas OL that are illuminated by the laser line marker 6a, instead the length of the overlapping imaging region OL (that is, the end-to-end distance of the area wherein adjacent imaging regions overlap, for example, the distance from the position A2 to the position B1 in FIG. 5) is short, and thus a center point of the overlapping image area may be illuminated. Note that the explanations of the parts that are redundant for those in the above example, described above, will be omitted. (The same is true in all of the examples.)

FIG. 6 will be referenced. The center point of the overlapping image area OL of adjacent imaging regions is illuminated by the laser line marker 6a. When the REHEARSAL button 22b of the operating panel 22 is pressed, the information that the REHEARSAL button 22b has been pressed is sent through the controlling portion 21 to the laser line marker emission controlling means 16. The laser line marker emission controlling means 16 illuminate the top end position t based on the position data for the plurality of partitioned regions, partitioned by the imaging region partitioning means 15. After this, based on information that the rehearsal button 22b has been pressed again, the center point C1 of the overlapping image area OL that is provided in the first imaging region and the second imaging region is illuminated. After this, similarly, the center point C2 of the overlapping image region that is provided in the second imaging region and the third imaging region is illuminated, and the position B3 (the bottom end position b) is illuminated.

Illuminating the center points of the overlapping image areas OL makes it possible to evaluate accurately whether or not an overlapping image area OL that is provided at adjacent imaging regions is provided at a location of interest of the examination subject M. Moreover, this is able to reduce the frequency of illumination further than in the method for illuminating the edge portions of the overlapping image areas OL.

Note that control may be performed so as to enable the operator to select either illumination of the edge portions of the overlapping image areas or illumination of the centers of the overlapping image areas as the particular location of the overlapping image area OL that is illuminated by the laser line marker 6a.

Figure 7:
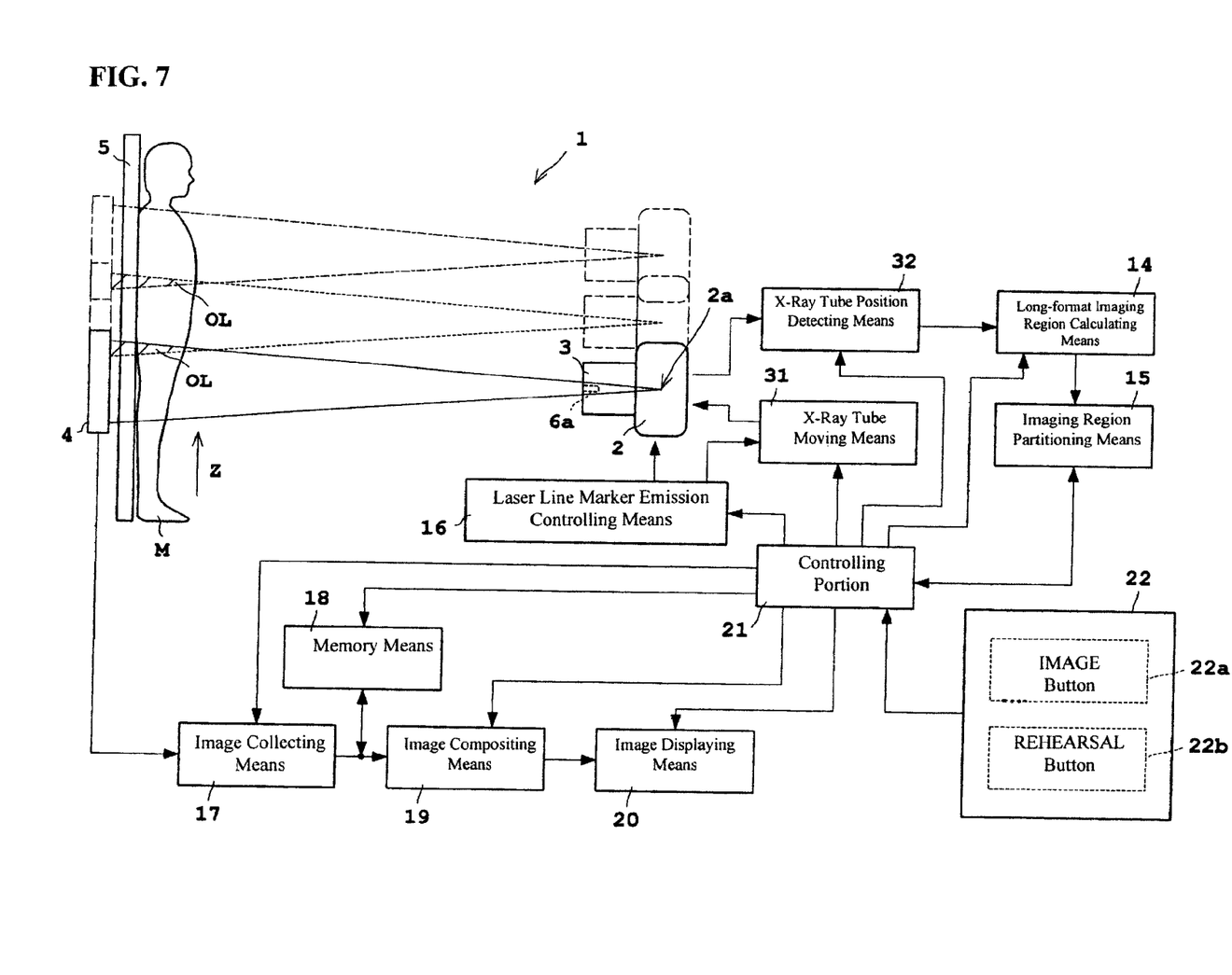
FIG. 7 is a schematic structural diagram illustrating an x-ray radiography device according to a further example.

A third example of embodiment of the present invention will be explained next referencing the figures. FIG. 7 is a schematic structural diagram illustrating an x-ray radiography device according to a further example of embodiment.

FIG. 7 will be referenced. The x-ray radiography device 1 described above is provided with x-ray tube angle changing means 11 for changing the angle of the x-rays and x-ray tube angle detecting means 12. This makes it possible to change the angle of the x-ray tube 2 around the focal point 2a in order to irradiate various positions, and to detect the angle of the x-ray tube 2. However, there is no limitation to this structure. X-ray tube moving means 31 for moving the x-ray tube 2 in, at least, the direction that is parallel to the bodily axis of the examination subject M, that is, in at least the direction that is parallel to the direction of linear motion of the FPD 4, and x-ray tube position detecting means for detecting the position of the x-ray tube 2 may be provided.

The respective positions are detected by the x-ray tube position detecting means 32 while the x-ray tube 2 is moved in the direction that is parallel to the direction of linear motion of the FPD 4, by the x-ray tube moving means 31, to illuminate, with the laser line marker 6a, the top end position t and the bottom end position b of the long-format image. The long-format imaging region L is determined thereby from the top end position t and the bottom end position b. After the long-format imaging region L is partitioned into a plurality of imaging regions, then, before x-ray imaging, the laser line marker emission controlling means 16 move the x-ray tube 2, by means of the x-ray tube moving means 31, to cause the laser line marker 6a to illuminate sequentially the particular locations in the overlapping image areas OL that are provided at adjacent imaging regions. This makes it possible for the operator to check each of the particular locations.

Figure 8:
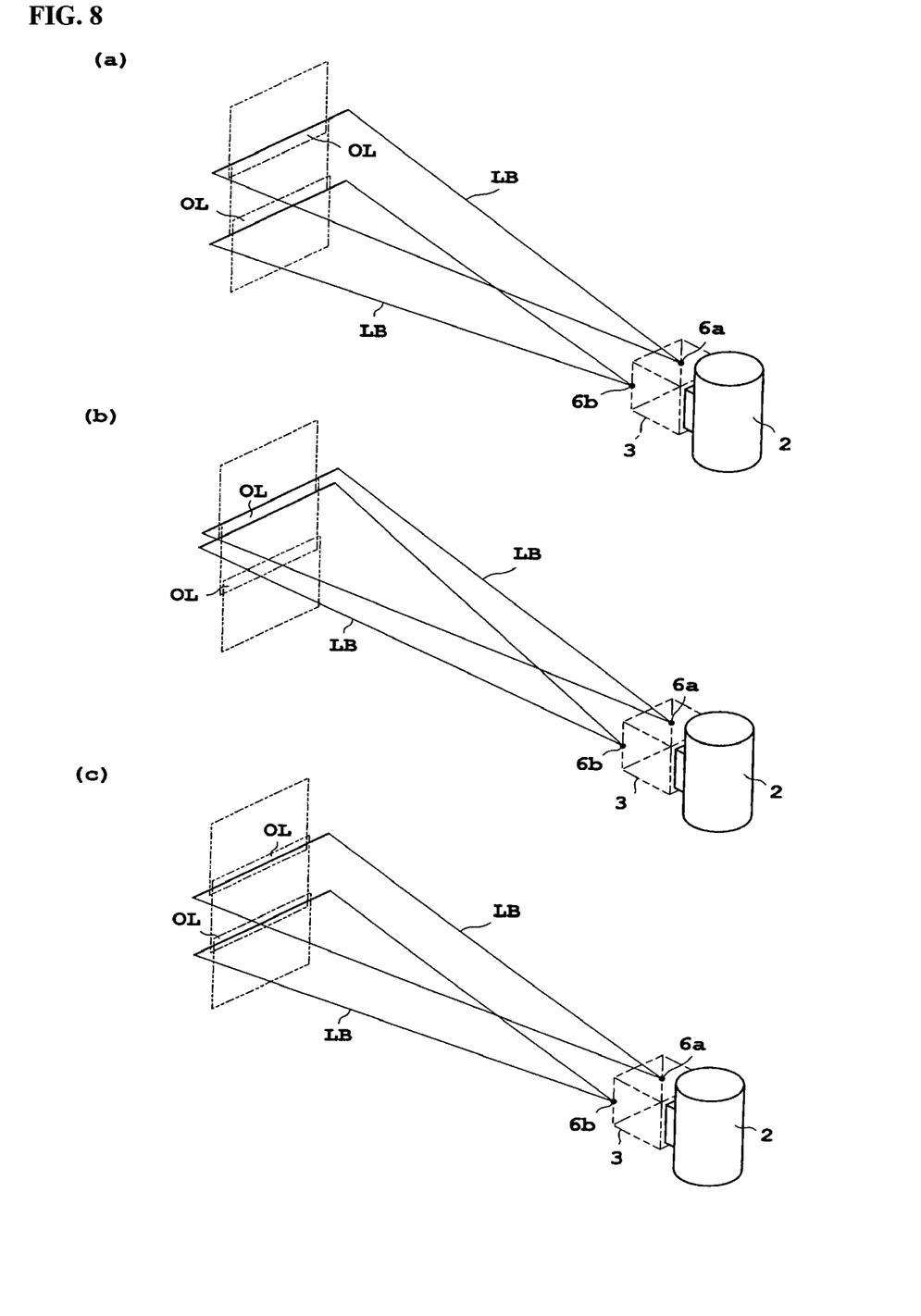
FIG. 8 is a perspective diagram for providing an explanation of the illumination of the laser line marker in yet another example, wherein (a) illustrates a case wherein both edge portions of the imaging region are illuminated, (b) illustrates a case wherein both edges of an overlapping image area are illuminated, and (c) illustrates a case wherein a center point of two overlapping image areas is illuminated.

Yet another example is explained next referencing the figures. FIG. 8 is a perspective diagram for providing an explanation of the illumination of the laser line marker in an example, wherein (a) illustrates a case wherein both edge portions of the imaging region are illuminated, (b) illustrates a case wherein both edges of an overlapping image area are illuminated, and (c) illustrates a case wherein a center point of two overlapping image areas is illuminated.

The x-ray radiography devices 1 set forth above are each provided with a single laser line marker 6a, where particular locations in the overlapping image areas OL were illuminated with the laser line marker 6a to enable checking as to whether or not the overlapping image areas OL that are provided at adjacent imaging regions are provided on locations of interest of the examination subject M. However, there is no limitation to this structure. The x-ray radiography device 1 may be structured with a plurality of laser line markers to illuminate respectively different positions of the overlapping image areas OL that are provided at adjacent imaging regions in the long-format imaging region may. The present example describes an x-ray radiography device 1 that is provided with two laser line markers 6a and 7d.

FIG. 8(a) will be referenced. The x-ray radiography device 1 is provided with a laser line marker 6a on the x-ray emitting side of the collimator 3 that is attached to the x-ray tube 2. A separate laser line marker 6b is also provided. In contrast to the laser line marker 6a, which is stationary, the laser line marker 6b is provided with means, not shown, for changing the direction of the emission thereof. As a result, the laser beam LB functions to emit in a direction that is different from that of the laser line marker 6a. Note that the structure may be one wherein the laser line marker 6b is provided in the x-ray radiography device 1 through means for changing the emission direction that are separate from the x-ray tube angle changing means 11.

The methods for illumination using these two laser line markers 6a and 6b may include, for example, the following. In FIG. 8(a), the laser line markers 6a and 6b illuminate sequentially both edge portions of each of the imaging regions into which the long-format imaging region L is partitioned. Each of the imaging regions can be checked thereby. In FIG. 8(b), the laser line markers 6a and 6b illuminate both ends of the overlapping image areas OL that are provided at adjacent imaging regions. This makes it possible to check the overlapping image areas. In FIG. 8(c), the laser line markers 6a and 6b illuminate the center points of the two overlapping image areas OL that are provided in the three continuous imaging regions. This makes it possible to check the positions of adjacent overlapping image areas.

Given this, the provision of the two laser line markers 6a and 6b make it possible to indicate respectively different particular locations of the overlapping image areas OL by the two laser markers 6a and 6b, thus making it possible to check two locations simultaneously. Doing so makes it possible to check accurately whether or not an overlapping image area OL is provided at a location of interest. Moreover, this enables the simultaneous illumination of different locations, making it possible to reduce the frequency of illumination.

Note that while in the structures set forth above in the examples of embodiment, the laser line marker 6a was stationary and the laser line marker 6b was provided with means, not shown, for changing the direction of emission thereof, instead both of the laser line markers 6a and 6b may be provided with means for changing the directions of emission thereof. Moreover, there is no limitation to 2, but rather three or more laser line markers may be provided.

The present invention is not limited to the examples set forth above, but rather may be enabled through modifications such as the following.

(1) While in the x-ray radiography devices 1 in each of the examples set forth above, the x-ray is emitted from an x-ray tube 2 that is disposed towards the side, facing an examination subject M in a standing posture, there is no limitation thereto. For example, the x-ray radiography device 1 may be one wherein the examination subject M lies on the top of a bed, and x-rays from an x-ray tube 2 that is disposed above the examination subject M may be directed at the examination subject M.

(2) While an FPD 4 was used as the x-ray detecting device in each of the examples set forth above, there is no limitation thereto. For example, an image intensifier (I. I.) may be used instead for the x-ray detecting device.

(3) While in each of the examples set forth above, the laser beam LB that was emitted from the laser line marker provided illumination in a line shape, there is no limitation thereto. For example, a laser line marker may be provided separate from the existing laser line marker, that is, laser beams LB that are emitted in line shapes from two laser line markers may be intersected and disposed so as to illuminate in the shape of a cross. For example, with two laser line markers as one set, one of the lines of the laser beam LB may be directed so as to be perpendicular, when viewed from the x-ray tube 2, relative to the bodily axis of the examination subject M, where a line of the other laser beam LB may be directed so as to pass through the bodily axis of the examination subject M, and may be directed not only at the edge portions, in the long-format direction that is parallel to the bodily axis, of the long-format imaging region L, but may also illuminate the corner portions of a rectangular illumination region to define clearly the edge portions in the crosswise direction as well.

(4) In the examples set forth above, the x-ray radiography device 1 is provided with a single laser line marker 6a in a state wherein it is attached rigidly to the collimator 3, so as to illuminate a particular location of the overlapping image area OL through changing the angle of the x-ray tube 2, or through moving the x-ray tube 2 in the direction that is parallel to the direction of movement of the FPD 4; however, there is no limitation thereto. For example, the structure may be one wherein means for changing the emission direction of the laser line marker 6a may be provided to illuminate particular locations of the overlapping image areas OL. Furthermore, the structure may be one wherein a laser line marker 6a is provided on the x-ray radiography device 1 through means for changing the emission direction that are separate from the x-ray tube angle changing means 11, to illuminate a particular location of the overlapping image area OL.

The invention claimed is:

1. An x-ray radiography device comprising:
   an x-ray tube emitting an x-ray toward an examination subject, with an attached collimator for adjusting the field of irradiation of the x-ray;
   an x-ray detection device detecting x-rays that have traversed the examination subject;
   a laser line marker emitting a laser beam that is emitted in the form of a line that, when viewed from the x-ray tube, is perpendicular to the bodily axis of the examination subject;
   a imaging region partitioning device partitioning, into a plurality of imaging regions, a long-format imaging region that has been set, so that there will be overlapping image areas wherein portions of adjacent imaging regions overlap; and
   a laser line marker emission controller controlling the emission of a laser beam from the laser line marker onto the overlapping image areas, by calculating the overlapping image areas based on location data for the plurality of imaging regions that have been partitioned by the imaging region partitioning means.

2. The x-ray radiography device as set forth in claim 1, wherein:
   the particular location of the overlapping image area is an edge portion of the overlapping image area.

3. The x-ray radiography device as set forth in claim 1, wherein:
   the particular location of the overlapping image area is an center point of the overlapping image area.

4. The x-ray radiography device as set forth in claim 1, further comprising:
   an x-ray tube angle changing device changing the direction of emission of a laser beam of the laser line marker by changing the angle of the x-ray tube around the focal point of the x-ray emission.

5. The x-ray radiography device as set forth in claim 1, further comprising:
   an x-ray tube moving device moving an emission location of a laser beam of the laser line marker by moving the x-ray tube in a direction that is parallel to the direction of movement of the x-ray detecting device.

6. The x-ray radiography device as set forth in claim 1, wherein:
   the laser line marker is structured from a plurality of laser line markers, and illuminates mutually different particular locations of the overlapping image areas.

* * * * *